US00PP25331P3

(12) United States Plant Patent
Skelton

(10) Patent No.: US PP25,331 P3
(45) Date of Patent: Mar. 10, 2015

(54) ***ACTINIDIA CHINENSIS* PLANT NAMED 'X264'**

(50) Latin Name: *Actinidia chinensis*
Varietal Denomination: X264

(71) Applicant: Donald Alfred Skelton, Huntly (NZ)

(72) Inventor: Donald Alfred Skelton, Huntly (NZ)

( * ) Notice: Subject to any disclaimer, the term of this patent is extended or adjusted under 35 U.S.C. 154(b) by 42 days.

(21) Appl. No.: 13/986,593

(22) Filed: May 15, 2013

(65) Prior Publication Data

US 2014/0345010 P1 Nov. 20, 2014

(51) Int. Cl.
*A01H 5/00* (2006.01)

(52) U.S. Cl.
USPC ..... Plt./156

(58) Field of Classification Search
USPC ..... Plt./156
See application file for complete search history.

*Primary Examiner* — Kent L Bell
(74) *Attorney, Agent, or Firm* — Cassandra Bright

(57) ABSTRACT

A new and distinct *Actinidia chinensis* cultivar named 'X264' is disclosed, characterized by having distinctive yellow flesh fruit, and an early seasonal harvest time. Additionally, the new variety produces oblong fruit with weak skin adherence to flesh and with a distinctive blunt, slightly protruding stylar end shape and square shoulders. The new variety is suitable for commercial production of kiwi fruit.

3 Drawing Sheets

Latin name of the genus and species: *Actinidia chinensis*.
Variety denomination: 'X264'.

BACKGROUND OF THE INVENTION

The new cultivar is a product of a planned breeding program under the direction of the inventor, Donald Alfred Skelton, a citizen of New Zealand. The seed parent is the unpatented, proprietary variety referred to as *Actinidia chinensis* 'A50'. The pollen parent is the unpatented, proprietary seedling variety referred to as *Actinidia chinensis* 'A28'.

Fruit of the new variety was first evaluated in 2001 with favorable results. After the first evaluation, semi-hardwood cuttings were made of 'X264' and were grafted onto seedling rootstocks of *A. deliciosa*. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'X264' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'X264' These characteristics in combination distinguish 'X264' as a new and distinct *Actinidia chinensis* cultivar:

1. Oblong shaped fruit form
2. Heavy fruit weight, similar to the known variety 'Hayward'.
3. Weakly blunt protruding stylar fruit end.
4. Yellow flesh fruit
5. early season fruit harvest
6. Weak adherence of fruit skin to flesh
7. Weak adherence of hair to fruit skin

COMMERCIAL COMPARISON

The new variety is best compared to the commercial variety, 'Hort16A' U.S. Plant Pat. No. 11,066. 'X264' is similar to 'Hort16A' in many horticultural characteristics, however, 'X264' produces mature fruit approximately 2 to 4 weeks earlier in the season than 'Hort16A'. Additionally, fruit of the new variety 'X264' has a weakly protruding stylar end, compared to the strongly protruding stylar end of 'Hort16A'.

The new variety can be compared to the commercial variety, 'Hayward', unpatented. 'X264' is similar to 'Hayward' in many horticultural characteristics, however, 'X264' produces mature fruit several weeks earlier in the season than 'Hayward'. Additionally, 'X264' has an interior fruit coloration with a stronger yellow tone.

The new variety is similar to the seed parent variety in some horticultural characteristics. However, the new variety differs in the following;

1. The new variety has a early-season bud set, compared to the late-season bud set of the seed parent.
2. The new variety flowers earlier than the seed parent variety.
3. Fruit of the new variety can be harvested earlier than fruit of the seed parent variety.

The new variety can be compared to the pollen parent variety, however, the plants clearly differ, as the new variety is a fruit producing female plant and the pollen parent is a non-fruiting male plant. The new variety differs in the following;

1. No fruit is produced by the pollen parent.
2. The new variety sets buds and flowers slightly earlier than the pollen parent.

BRIEF DESCRIPTION OF THE PHOTOGRAPH

The accompanying photograph in FIG. 1 illustrates in full color examples of typical flowers of 'X264'.

Figure 1:
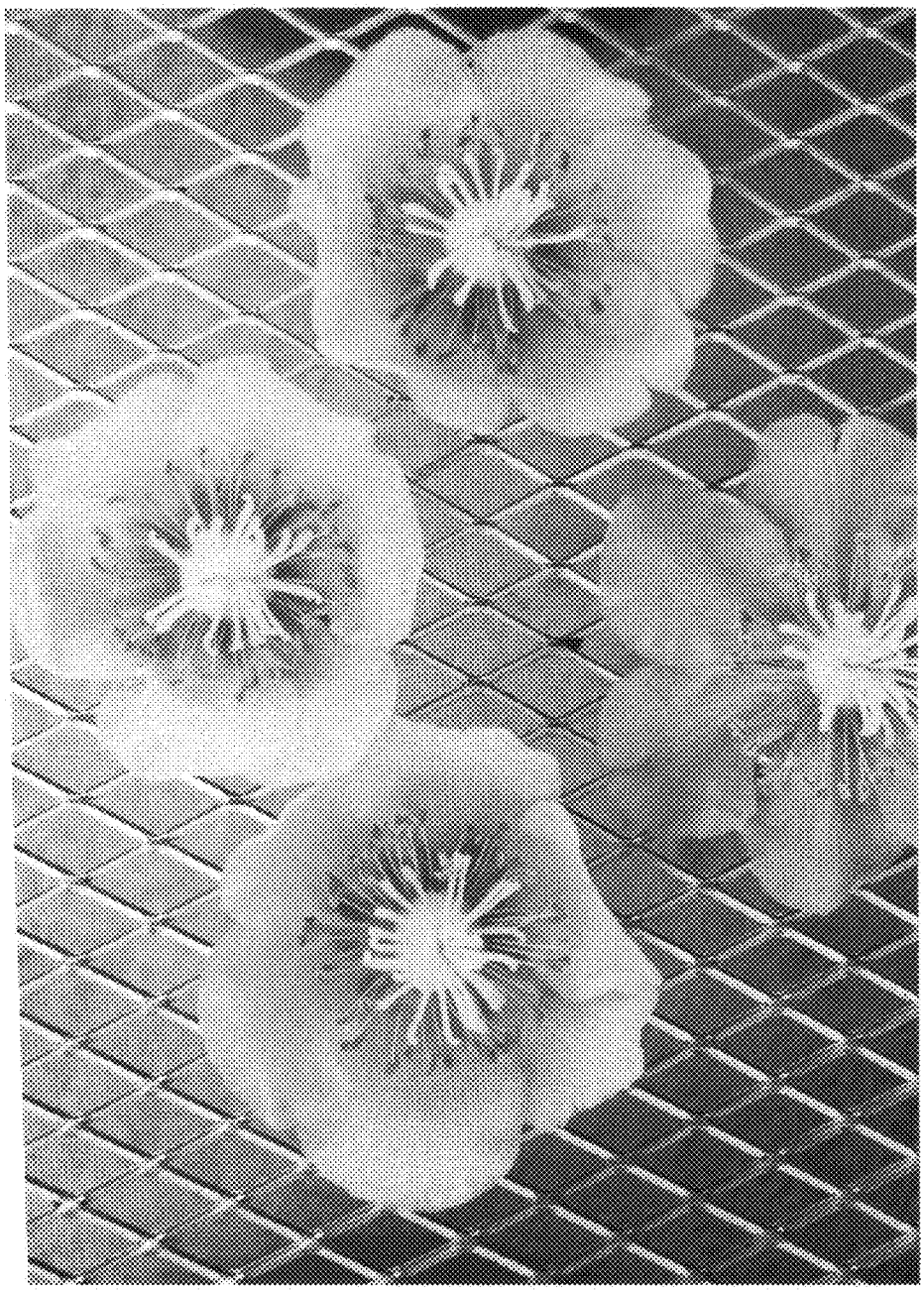
Figure 2:
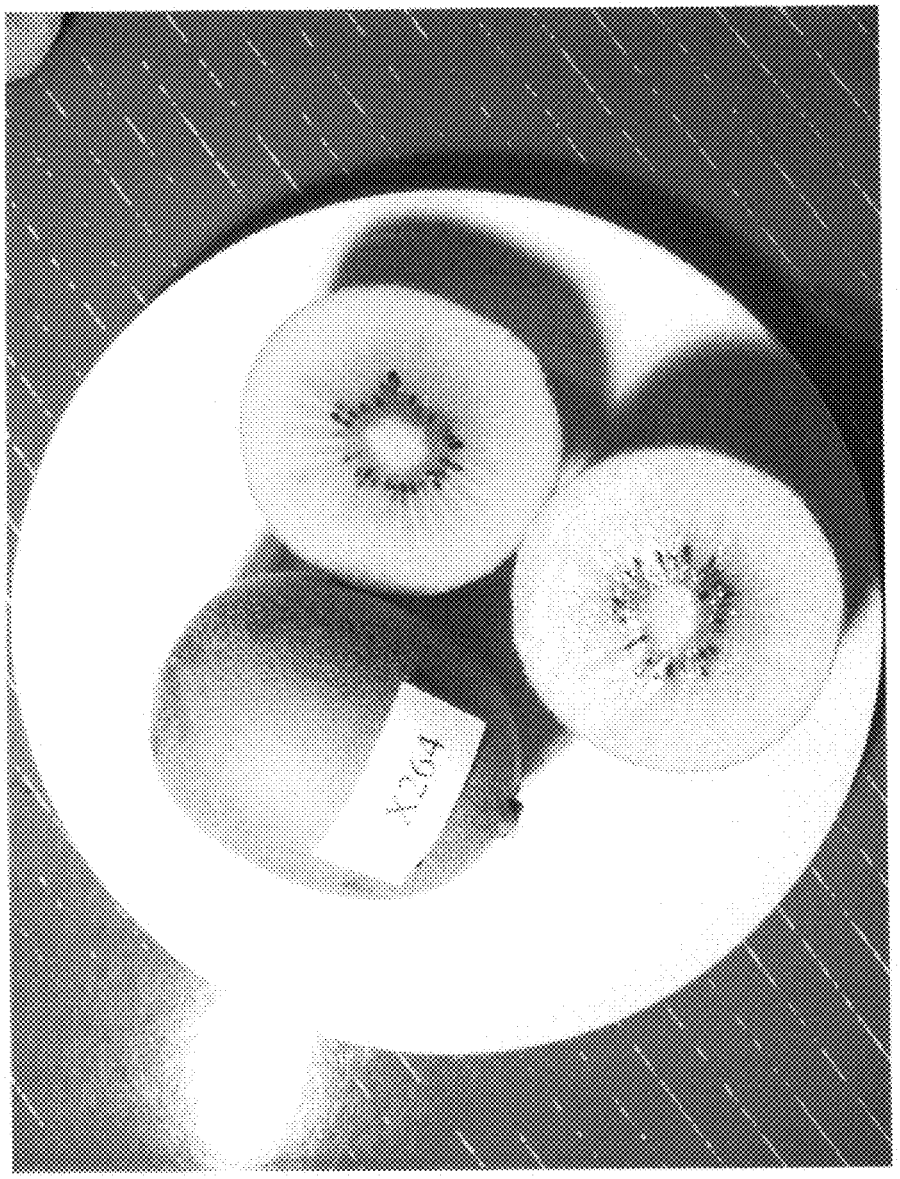
FIG. 2 illustrates fruit harvested from 'X264'.
Figure 3:
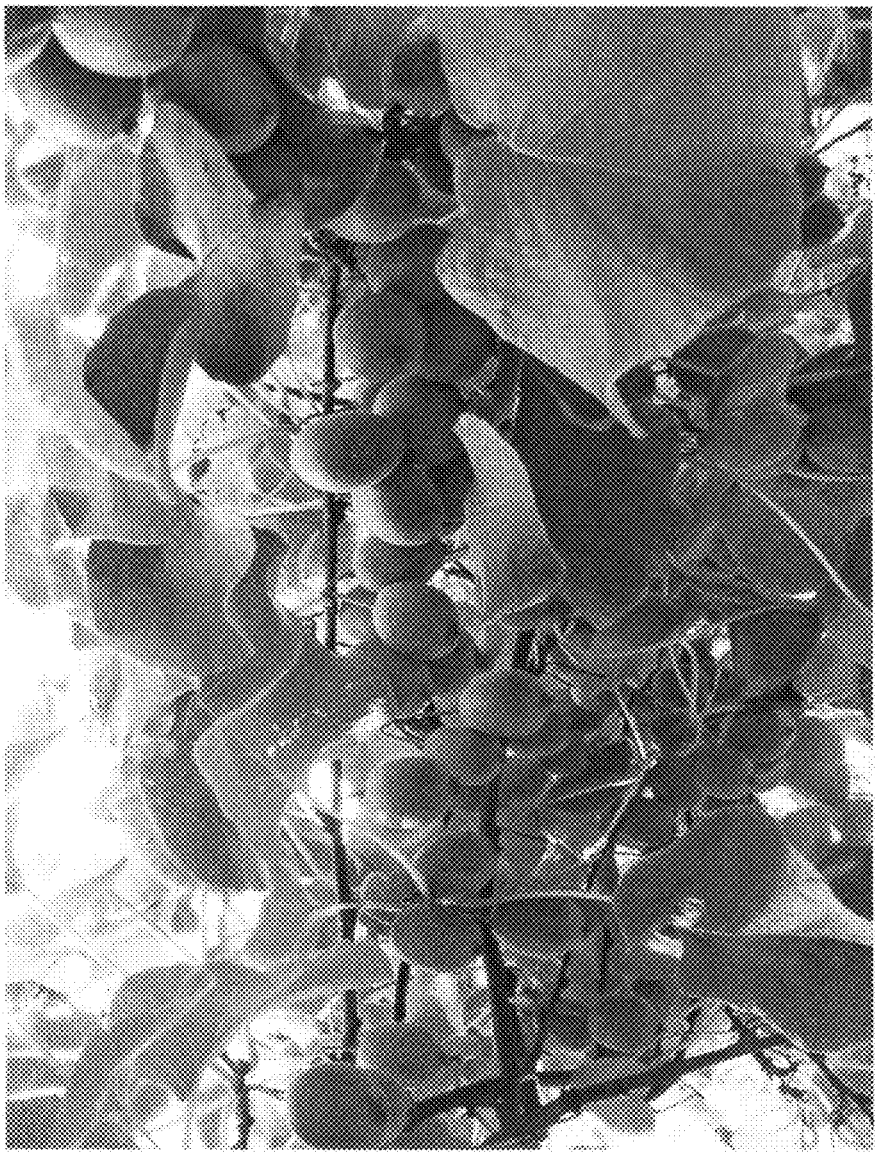
FIG. 3 illustrates in full color typical foliage, hanging fruit and stems on plants of 'X264'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'X264' plants grown outdoors under commercial trial conditions in North Waikato, New Zealand. The growing temperature ranged from 10° C. to 30° C. during the day and −4° C. to 18° C. at night. Annual rainfall is approximately 125 cm per year. Measurements and numerical values represent an average of 10 typical plant types.

Botanical classification: *Actinidia chinensis* 'X264'.

PROPAGATION

'X264' can be successfully grafted onto rootstocks of *Actnidia deliciosa.*

PLANT

*Age of the plant described.*—Approximately 5 years.
*Average width.*—Canopy is an average of 300 cm by 400 cm to 500 cm by 500 cm. Canopy is pruned to industry standard sizing.
*Sex expression.*—Female.
*Ploidy.*—Diploid.
*Vigor.*—Moderate.
*Young shoot texture.*—Glabrous.
*Trunk diameter.*—Approximately 5.0 cm for a 6 year old vine.
*Young shoot color.*—Near RHS Yellow-Green 144C.

Stem characteristics:
*Color.*—Near RHS Brown 200D on upper (sunny side) surface. Lower surface Yellow-Green 144C.
*Stem diameter.*—Average 1.5 cm.
*Stem length.*—Average range 100 to 200 cm.
*Stem texture.*—Smooth, non-pubescent with a moderate amount of very minute lenticels.
*Stem pith.*—Solid.
*Lenticel description.*—Length: Average 0.25 cm. Width: Average 0.1 cm. Density: Approximately 15 per 5 cm of stem.
*Leaf scar description.*—Moderately depressed.

FOLIAGE

Leaf:
*Average length.*—16 cm.
*Average width.*—18 cm.
*Shape of blade.*—Obovate.
*Apex.*—Retuse.
*Base.*—Cordate, basal lobes not touching.
*Attachment.*—Petioled.
*Margin.*—Mildly ciliate.
*Texture of top surface.*—Very slightly puckered. Non-pubescent.
*Texture of under side.*—Non-pubescent.
*Color.*—Mature foliage upper side: Near RHS Green 137A. Mature foliage under side: Near RHS Green 138C.
*Petiole.*—Length: Average length 17.5 cm. Diameter: Approximately 0.6 cm. Texture: Glabrous. Pubescence: None. Color: Upper Surface near RHS Yellow-Green N143D. Moderate anthocyanin on upper side only, near Greyed-Purple 184D.

FLOWER

*Flowers per inflorescence.*—Normally 3.
*Bud color.*—Near RHS Yellow-Green 145A.
*Bud shape.*—Oblong.
*First flower.*—Early Pollinized by proprietary varieties referred to as 'A55', 'CMWW85' and 'CMW53'.
*Diameter.*—Average 6 cm.
*Depth.*—Average 3.6 cm.
*Petal quantity.*—6 to 10 per flower.
*Petals overlapping.*—Yes.

Petals:
*Length.*—Approximately 3.1 cm.
*Width.*—Approximately 2.1 cm.
*Shape.*—Broad spatulate.
*Aspect.*—Upwardly cupped.
*Margin.*—Entire.
*Texture.*—Glabrous, all surfaces.
*Base.*—Truncate.
*Apex.*—Obtuse.
*Petal color.*—Near RHS Yellow-White 158D upper and lower surfaces.
*Filament color.*—Near RHS Green-White 157D.
*Anther color.*—Near RHS Yellow-Orange 163A.
*Attitude of styles.*—Semi-erect.
*Style color.*—Near RHS White 155A.
*Style quantity.*—Average 20.
*Hair on ovary.*—Dense.
*Color of ovary.*—Near RHS White 155A.
*Number of sepals.*—6 to 10.
*Color of sepals.*—Near RHS Green 144B upper and lower surfaces.
*Sepal width.*—Approximately 1 cm.
*Sepal length.*—Approximately 1.3 cm.
*Sepal texture.*—Smooth.
*Sepal shape.*—Deltate.
*Sepal margin.*—Entire.
*Sepal apex.*—Acute.
*Sepal base.*—Truncate.

Peduncle:
*Length.*—Average 6.6 cm.
*Diameter.*—Average 0.5 cm.
*Color.*—Near RHS Green 144B.
*Texture.*—Smooth.

FRUIT

*Average weight.*—97 grams.
*Average length.*—6.2 cm.
*Average diameter.*—5.0 cm.
*Color outer pericarp.*—Near RHS Yellow 5D.
*Color inner pericarp.*—Near RHS Yellow 4A.
*Core color.*—Near RHS Yellow 5C.

*Core diameter*.—Average 1.0 cm.
*General shape*.—Oblong.
*Median cross section*.—Circular.
*Stylar end shape*.—Weakly blunt protruding.
*Shoulder shape*.—Squared, truncate.
*Calyx ring*.—Present.
*Calyx ring expression*.—Strong.
*Skin color at harvest*.—Near RHS Yellow-Green 152C.
*Hair on fruit skin*. —Downy.
*Hair adherence to skin*.—Weak.
*Skin adherence to flesh at maturity*.—Weak.
*Fruit core shape*.—Transversely elliptic.
*Core-woody spike*.—Small.
*Lenticels on fruit*.—Lenticels absent on fruit.
*Locules*.—Quantity per fruit: 27 to 28. Length: Average range 1.3 to 1.5 cm. Width: Highly variable, no typical range. Color: Near RHS Green-Yellow 1A.
*Mature seed color*.—Black.
*Dried seed*.—Brown.
*Harvest time*.—Early season.

OTHER CHARACTERISTICS

Storage life: Storage life is a minimum of 3 months at 2° C.
Disease/pest resistance: Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'X264' as herein illustrated and described.

* * * * *